(12) United States Patent
Blacklock et al.

(10) Patent No.: US 6,179,615 B1
(45) Date of Patent: Jan. 30, 2001

(54) DENTAL DRILL WITH INTEGRAL GUIDE

(76) Inventors: Gordon D. Blacklock, 14116 Grand NE., Albuquerque, NM (US) 87123; Americo Fernandes, 1-2055 McPhillips Street, Winnipeg, Manitoba (CA), R2V 3C6

( * ) Notice: Under 35 U.S.C. 154(b), the term of this patent shall be extended for 0 days.

(21) Appl. No.: 09/277,200

(22) Filed: Mar. 26, 1999

(51) Int. Cl.[7] ................................................. A61C 3/02
(52) U.S. Cl. ......................................... 433/165; 408/209
(58) Field of Search .................................. 433/165, 166; 408/209, 225

(56) References Cited

U.S. PATENT DOCUMENTS

| | | | |
|---|---|---|---|
| 770,115 | * 9/1904 | Rood | 433/165 |
| 1,123,730 | * 1/1915 | Greenfield | 433/165 |
| 1,216,683 | 2/1917 | Greenfield | 433/165 |
| 1,333,388 | 3/1920 | Chester | 433/165 |
| 2,453,696 | * 11/1948 | Brooks | 433/165 |
| 2,807,264 | * 9/1957 | Tuck | 433/166 |
| 4,787,848 | 11/1988 | Ross | 433/165 |
| 5,098,293 | 3/1992 | Lööf et al. | 433/165 |
| 5,100,322 | * 3/1992 | Weissman | 433/165 |

FOREIGN PATENT DOCUMENTS

| | | | |
|---|---|---|---|
| 105540 | * 1/1899 | (DE) | 433/165 |
| 500538 | * 6/1930 | (DE) | 433/166 |

* cited by examiner

Primary Examiner—John J. Wilson
(74) Attorney, Agent, or Firm—Siemens Patent Services, LC

(57) ABSTRACT

A drill particularly suited for drilling holes for dental anchors. The drill has a central shaft including a proximal end having conventional connection structure for attachment to a powered rotatable appliance and a distal end bearing a forwardly projecting pin which occupies and is guided within a pilot bore. The pin has a blunt, preferably spherical, enlarged head. The blade is mounted on the central shaft between the proximal and distal ends of the shaft. The blade is preferably annular, having cutting teeth facing the distal end of the shaft. At least one relief communicates between the interior of the annular blade and the exterior thereof.

8 Claims, 2 Drawing Sheets

DENTAL DRILL WITH INTEGRAL GUIDE

BACKGROUND OF THE INVENTION

1. Field of the Invention

The present invention relates to drills, and more particularly to a drill having a support pin which is received in a pilot hole. This feature enables the drill to be pivoted somewhat as the blade bears against material being cut. The novel drill finds utility in applications wherein it is desirable to incline the drill while bearing down on the cutting blade. A principal contemplated use is in the field of dental anchors, wherein gum tissue must be cut away to install the anchor, and osteosurgery, wherein pins and other members must be inserted into bone tissue. However, the novel drill would be useful in many settings wherein the angle of the cut must be varied from that of the pilot hole. Illustratively, it may be necessary in repair and restoration work in fields other than dental and medical fields to accommodate localized areas of material which is not of sufficient strength and good condition to receive fasteners or otherwise support members being attached.

2. Description of the Prior Art

From time to time, it becomes necessary to install external members into a material which has deteriorated over time or with exposure to a deleterious influence. Frequently, localized conditions cannot be determined until the material is exposed by cutting. In the field of installing dental anchors in the jaw, the most advantageous angle at which the anchor is to be oriented may not be susceptible of being determined until actual drilling commences. If the dental practitioner drills a pilot hole, then he or she is constrained to the angle of the pilot hole. Should local conditions at the jaw require adjustment in drilling angle, then rigidity of the process threatens the quality of the remedial therapy.

A dental drill is shown in U.S. Pat. No. 4,787,848, issued to Stanley E. Ross on Nov. 29, 1988 having a circular cutting blade. There is no guide pin as seen in the present invention.

U.S. Pat. No. 5,098,293, issued to Lennart Lööf et al. On Mar. 24, 1992, describes a machining device for implant work which device has a machining blade formed as a spherical member located at the end of a shaft. Although this configuration bears a superficial similarity to the preferred embodiment of the present invention, a significant difference exists in that the spherical member of the present invention is blunt and not capable of cutting. Also, the present invention has a circular blade located above the spherical member. By contrast, the spherical member of Lööf et al. is the blade, and no annular blade is present in the device of Lööf et al.

U.S. Pat. No. 1,216,683, issued to Edwin J. Greenfield on Feb. 20, 1917, describes a hole cutting saw intended for dental implants. The saw has an annular blade bearing teeth and has relief holes formed in the blade. There is neither a support pin projecting forwardly of the cutting edge of the blade, nor an enlarged blunt head located forwardly of the cutting blade, both being features of the present invention.

U.S. Pat. No. 1,333,388, issued to William E. Chester on Mar. 9, 1920, illustrates a dental drill having a fluted drill bit projecting ahead of an annular hole cutting blade. The fluted bit drills a pilot bore ahead of the hole cutting blade, but could not accommodate inclination of the hole cutting blade relative to the pilot hole as occurs in the present invention.

None of the above inventions and patents, taken either singly or in combination, is seen to describe the instant invention as claimed.

SUMMARY OF THE INVENTION

The present invention provides a hole cutting blade which has a projecting support pin at its distal end. The pin is received in a pilot bore drilled into the jaw. The support pin terminates in an enlarged, generally spherical head. The shaft of the pin is of a diameter reduced from that of the head. This relationship enables the cutting blade assembly to be inclined out of alignment with the axis of the pilot bore. When drilling, a dental practitioner is thus afforded an opportunity to adjust direction and orientation of the hole generated by the annular blade. This is especially important in those instances wherein local conditions at the jaw make it desirable to make such an adjustment. No prior art tool affords this ability.

The enlarged head is blunt, so as not to extend the pilot hole beyond its original depth, or to abrade or pulverize tissue. The shape is preferably spherical so that the novel drill is readily rotated and inclined to a new position within the pilot bore. The support pin is generally aligned with the pilot bore, with slight deviation accommodated by virtue of the enlarged head being of greater diameter than the shaft of the support pin.

The cutting blade is preferably annular, having a cutting surface facing the enlarged head of the support pin. The blade has at least one relief opening communicating between the interior of the annular blade and the exterior thereof, for enabling expulsion of drilling detritus from the interior of the blade. The cutting blade is sharp enough to cut through soft gum tissue, but will not readily cut through bone tissue. The blade is therefore self-stopping.

At its proximal end, the shaft of the drill bears conventional attachment structure so that the drill can be mounted in a conventional powered driving appliance to rotate the drill under power.

Accordingly, it is one object of the invention to provide a drill which seats and supports itself in a pilot hole without drilling the pilot hole deeper.

It is another object of the invention to provide a drill capable of being inclined from a pilot hole in which it is received.

Another object of the invention is to enable the drill to expel drilling detritus.

It is a further object of the invention to enable the novel drill to be employed with a conventional rotating driving appliance.

Still another object of the invention is to enable a dental practitioner to modify the angle of a hole being drilled from that of an associated pilot hole.

An additional object of the invention is to prevent a dental drill from penetrating excessively into tissue being drilled.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
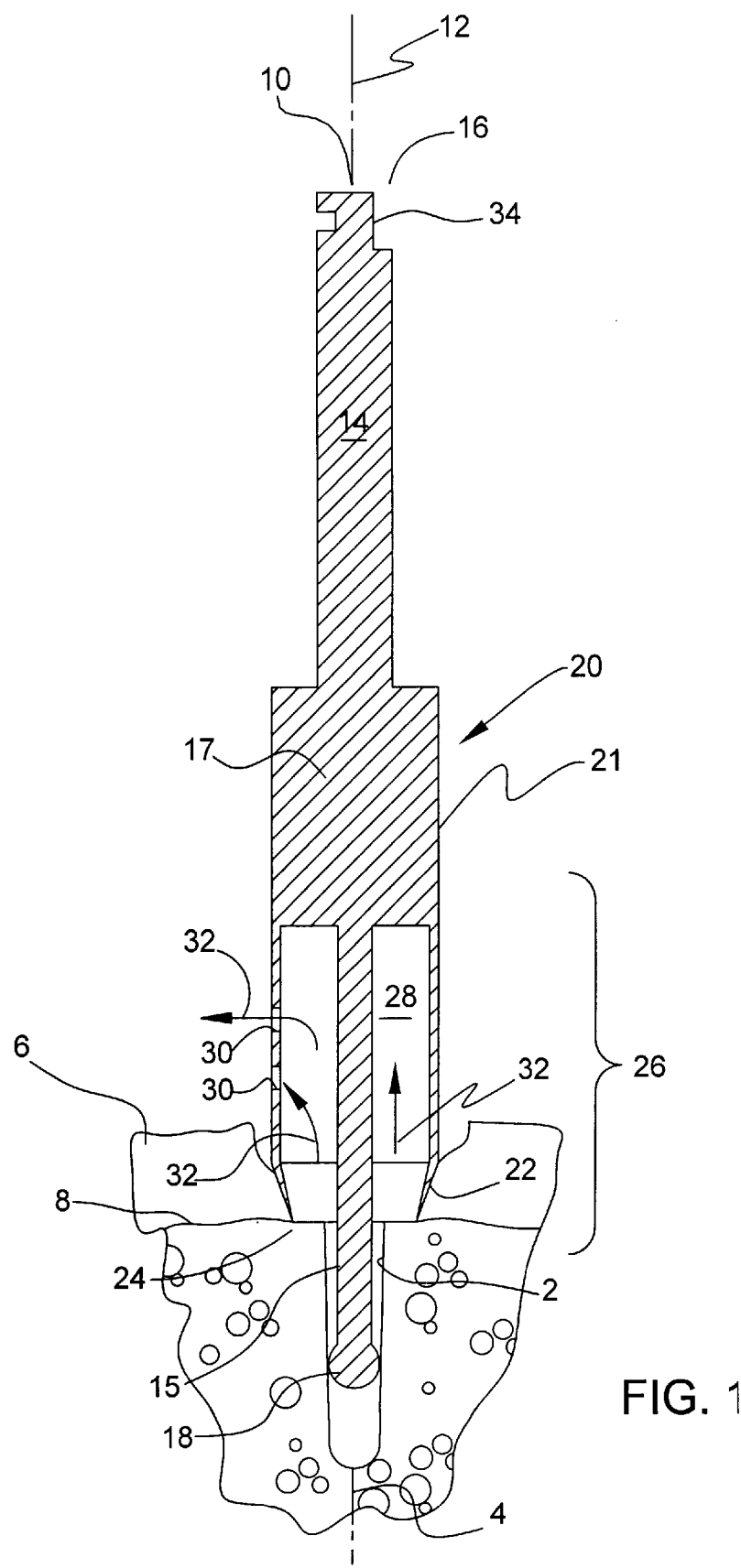
FIG. 1 is an environmental, cross sectional view of the invention.

FIG. 1 of the drawings shows a drill 10 which is particularly suitable for use with a powered rotatable driving appliance (not shown). Drill 10 can be inserted into a pilot bore 2 formed in a base material such as gum tissue 6 being drilled and slightly inclined from a coaxial relationship with pilot bore 2. Gum tissue 6 extends downwardly to bone tissue 8. It will be seen that center line 4 of pilot bore 2 is not coaxially aligned with center line 12 of drill 10. This relationship illustrates the principal advantage of novel drill 10.

Drill 10 comprises a central shaft 14 having a proximal end indicated generally at 16 and a distal end characterized by a blunt head 18. As seen in the cross sectional view of FIG. 1, shaft 14 is continuous and solid along its length. Head 18 is supported on that portion of shaft 14 forming support pin 15. Pin 15 is that portion of shaft 14 extending downwardly from the base 17 of a cutting blade 20. Cutting blade 20 is disposed around and fixed to shaft 14 between the proximal and distal ends of shaft 14. Blade 20 has a sharp cutting surface 22 bearing teeth 24 (see also FIG. 2). Cutting blade 20 has an outer lateral surface 21 devoid of teeth. Cutting surface 22 and teeth 24 are located at the bottom of an annular cutting portion 26 of blade 20.

Annular cutting portion 26 has an interior 28 which can become clogged with detritus accumulated by drilling. Two relief passages 30 are formed in the annular cutting portion 26 of blade 20 so that detritus can be cleared to the outside of blade 20. Relief passages 30 communicate between interior 28 of blade 20 and the exterior thereof. Arrows 32 indicate flow through passages 30 of detritus removed from base material 6 when cutting. Teeth 24 are configured to resist cutting when a hard surface such as that presented by bone tissue 8 is encountered.

Shaft 14 has keyed configuration at proximal end 18. Keyed configuration signifies any configuration which will oppose ineffectual rotation relative to a driving appliance (not shown) when drill 10 is coupled to the appliance. In the embodiment of FIG. 1, the keyed configuration is a flat surface 34 formed in the otherwise cylindrical configuration of shaft 14. A circumferential groove 36 is also formed at proximal end 16. Flat surface 34 and groove 36 are employed to couple drill 10 to a conventional driving appliance enabling drilling of material 6.

Figure 2:
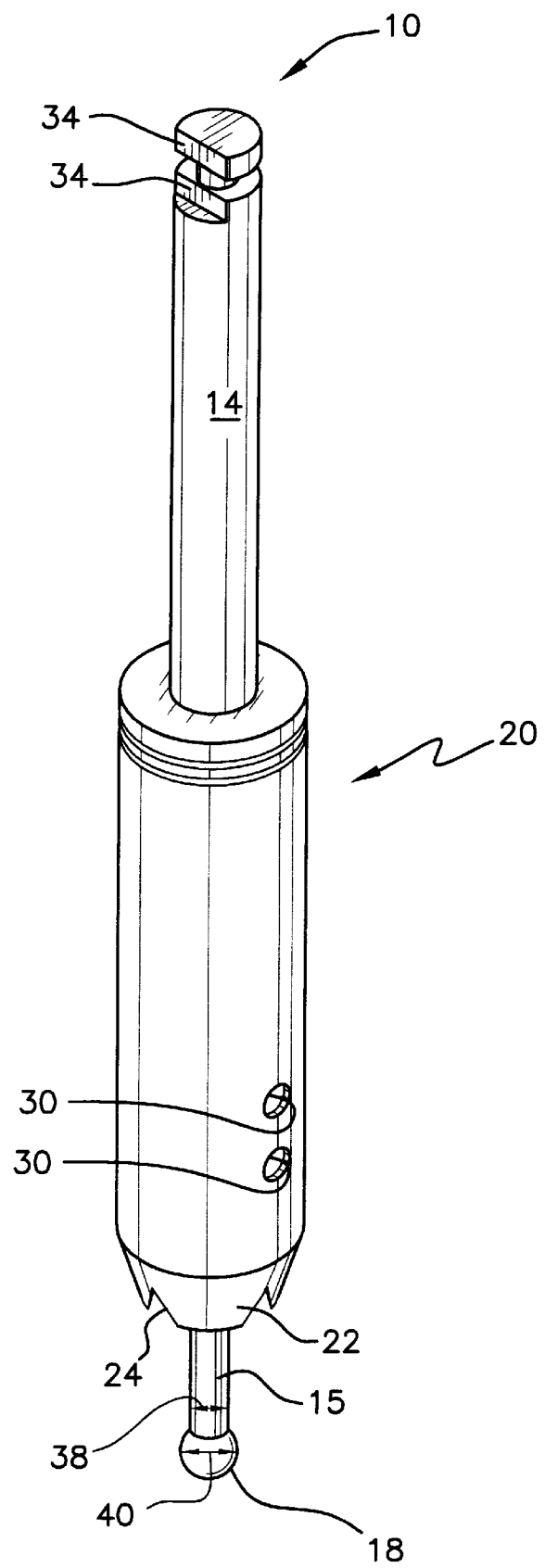
FIG. 2 is a perspective view of the invention.

FIG. 2 clearly shows flat surface 34, passages 30, cutting surface 22, and teeth 24. It will be seen that shaft 14 has a first diameter indicated at 38. Head 18 has a second diameter indicated at 40. Magnitude of diameter 40 is greater than that of diameter 38. This relationship accommodates inclination of drill 10 relative to pilot bore 2, as shown in FIG. 1.

Head 18 is mostly spherical apart from where it connects to pin 15. Although other blunt configurations preferably including smooth curves would be acceptable to operation of drill 10, spherical configuration is preferred. Blunt configurations, if employed, could include variable radius curves and even irregular shapes (neither shown).

It is to be understood that the present invention is not limited to the embodiments described above, but encompasses any and all embodiments within the scope of the following claims.

We claim:

1. A drill for use with a powered drill rotating appliance for cutting soft gum tissue, wherein said drill can be inserted into a pilot bore and slightly inclined from a coaxial relationship with the pilot bore, comprising:

a central shaft having a proximal end and a distal end, said distal end having a blunt head, wherein said central shaft is continuous and solid along its entire length; and a cutting blade disposed upon and fixed to said shaft between said proximal end and said distal end of said shaft, wherein said cutting blade has a sharp edge for cutting said soft gum tissue and being located at the bottom of said cutting blade and facing said distal end of said shaft and a smooth outer lateral surface.

2. The drill according to claim 1, wherein said central shaft has a first diameter, and said head of said central shaft has a second diameter greater in magnitude than that of said first diameter.

3. The drill according to claim 1, wherein said head of said central shaft is mostly spherical.

4. The drill according to claim 1, wherein said shaft has keyed configuration at said proximal end.

5. The drill according to claim 1, wherein said shaft has a circumferential groove at said proximal end.

6. The drill according to claim 1, wherein said cutting blade includes an annular cutting portion having an interior and an exterior.

7. The drill according to claim 6, wherein said cutting blade has a relief passage communicating between the interior of said annular cutting portion and the exterior of said annular cutting portion.

8. A drill for use with a powered drill rotating appliance for cutting soft gum tissue, wherein said drill can be inserted into a pilot bore and slightly inclined from a coaxial relationship with the pilot bore, comprising:

a central shaft having a proximal end and a distal end, wherein said central shaft is continuous and solid along its entire length, said distal end having a mostly spherical head, wherein said central shaft has a first diameter, and said head of said central shaft has a second diameter greater in magnitude than that of said first diameter, and said proximal end having keyed configuration and a circumferential groove disposed at said proximal end; and a cutting blade disposed upon and fixed to said shaft between said proximal end and said distal end of said shaft, wherein said cutting blade includes an annular cutting portion having a bottom, said cutting portion including a sharp edge for cutting said soft gum tissue and being located at said bottom and facing said distal end of said shaft, and a smooth outer lateral surface, and a relief passage communicating between the interior of said annular cutting portion and the exterior of said annular portion.

\* \* \* \* \*